United States Patent [19]

Tedesco

[11] Patent Number: 4,978,182

[45] Date of Patent: Dec. 18, 1990

[54] LASER PROTECTION VISOR WITH ELLIPSOIDAL GEOMETRY

[75] Inventor: James M. Tedesco, Livonia, Mich.

[73] Assignee: Kaiser Optical Systems, Ann Arbor, Mich.

[21] Appl. No.: 425,698

[22] Filed: Oct. 23, 1989

[51] Int. Cl.$^5$ .............................................. G02B 5/32
[52] U.S. Cl. ...................................... 350/3.7; 351/44; 2/432
[58] Field of Search .................. 350/1.6, 3.6, 3.7, 3.72, 350/164, 166, 278, 279, 311, 600, 601, 629, 630, 642; 351/44; 2/431, 432, 8

[56] References Cited

U.S. PATENT DOCUMENTS

| | | | |
|---|---|---|---|
| 3,519,339 | 7/1970 | Hutchinson et al. | 351/44 |
| 4,637,678 | 1/1987 | Moss et al. | 350/3.7 |
| 4,786,125 | 11/1988 | Magarinos et al. | 351/44 |
| 4,830,441 | 5/1989 | Chang | 350/3.77 |

*Primary Examiner*—Bruce Y. Arnold
*Assistant Examiner*—J. P. Ryan
*Attorney, Agent, or Firm*—Krass & Young

[57] ABSTRACT

The present invention is a laser protection visor. This visor has an ellipsoidal shape. The major axis of the ellipsoid falls on the line connecting the user's eyes. The foci least as far apart as the expected interpupillary distance of the user. The visor has a modulated index of refraction reflection filter disposed thereon having a rejection bandwidth including the wavelength of the expected laser threat. The ellipsoidal shape minimizes the maximum rejection angle needed to prevent laser radiation from reaching either eye. This in turn minimizes the needed rejection bandwidth and thus increases the visual see through at other wavelengths. In the preferred embodiment the modulated index or refraction layer forming the reflection filter is formed of a holographic optical element constructed by capturing an interference pattern in a photosensitive medium. In an alternative embodiment, the visor has an ellipsoidal center segment and peripheral segments which deviate from an ellipsoidal shape in a manner permitting the maximum needed rejection angle at any portion of the peripheral segments to be no greater than the maximum rejection angle needed at the center of the ellipsoidal segment.

15 Claims, 5 Drawing Sheets

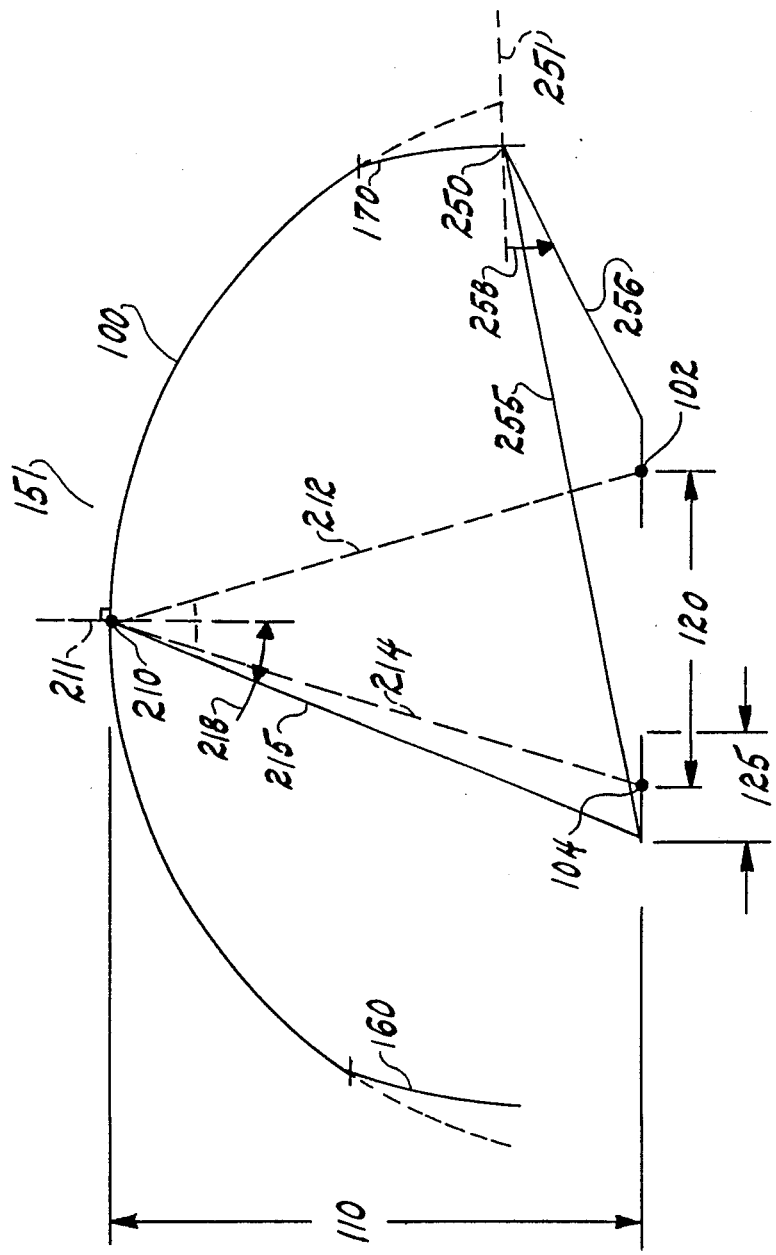

LASER PROTECTION VISOR WITH ELLIPSOIDAL GEOMETRY

TECHNICAL FIELD OF THE INVENTION

The technical field of the present invention is that of laser protection and in particular laser eye protection in the form of a helmet visor.

BACKGROUND OF THE INVENTION

Due to recent advances in the technology of laser generation and detection, laser systems for use in battlefield conditions have become more and more prevalent. These laser systems are employed for target illumination and tracking or ranging. Such laser systems may also be employed for intentional blinding of personnel or sensors. In a particular battlefield setting, there may be numerous laser illuminators operating simultaneously. These laser illuminators may be both from friendly forces and from enemy forces. In particular, combat troops such as aircraft pilots operating in this environment will be subject to uncontrolled illumination by laser radiation. Because of the great radiated power from these laser radiation sources, these personnel require some eye protection from this laser illumination.

There have heretofore been suggested numerous solutions for this problem of laser protection. In particular, in recent years there has been an increased interest in the development of modulated index of refraction filter elements as laser protection devices. Modulated index of refraction filter elements include 3-dimensional modulated index of refraction patterns which reflect light by diffraction at specified wavelengths. Such modulated index of refraction filter elements may be constructed of multilayer dielectric filters or of holographic optical elements. Multilayer dielectric filters are typically constructed from transparent layers of differing indices of refraction vapor deposited on a substrate. Holographic optical elements are ordinarily constructed employing laser illumination to form interference fringes within the volume of a photosensitive medium. Upon development of the photosensitive medium, the pattern of the interference fringes is fixed within this medium in the form of varying indices of refraction. When light of certain wavelengths enters such a modulated index of refraction filter element, it is diffracted by the modulated index of refraction pattern.

In the case of laser protection eyewear, it is common to form a reflection holographic optical element which reflects incoming radiation at the particular wavelength in a manner making it appear to be a mirror. Because the known laser generators employed in the combat environment include a relatively limited number of wavelengths, it is possible to form a holographic optical element for protection at each wavelength. The laser protective eyewear becomes, in effect, a reflection filter having a relatively narrow filter band about the expected wavelength of the laser source. It is possible to construct a compound structure including holographic optical elements constructed to reflect differing wavelengths disposed in tandem, in order to provide protection for a number of differing laser sources. Because the width of the notch in such holographic optical element reflectors is relatively narrow, normal visibility through such laser protective eyewear, even such eyewear having multiple holographic optical elements for protection against a number of wavelengths, is relatively unimpaired.

Structures heretofore employed in such laser eye protection devices as goggles or visors do not solve all the problems of laser protection. In particular, it is known in the art that such holographic optical elements, do not provide protection for all angles of incident radiation. These reflection holographic optical elements provide a protection over only a cone of incident angles. Thus, the eye is not protected from laser illumination received at angles of incidence outside this cone. In the case of goggles or visors, it is possible to provide laser protection for greater angles of incidence employing construction geometries related to the expected position of the eye.

U.S. Pat. No. 4,637,678, issued to Moss et al. on Jan. 20, 1987 entitled "Holographic Laser Protection Device," teaches compound holographic optical element structure. A first holographic optical element covers angles of incidence about the normal to the surface of the visor, and a second holographic optical element covers angles of incidence oblique to the surface of the visor. In a second embodiment taught in that patent, the elements in a compound holographic optical element structure offer complementary coverage for angles of incidence from the right and from the left.

In U.S. Pat. No. 4,830,441 issued May 16, 1989 entitled "Holographic Filter Construction for Protective Eyewear," having the same assignee as the present invention, the geometry of the laser protection eyewear relative to the eye is exploited to provide greater angular coverage. This patent teaches the use of virtual geometries which are spherically symmetrical about the center of the eye rather than spherically symmetrical about the center of curvature of the protective element as previously taught.

These prior developments fail to provide an adequate design for a laser protection helmet visor for an aircraft pilot. Thus it is a need in the art to provide laser eye protection simultaneously for both eyes for all possible angles of incidence to each eye.

SUMMARY OF THE INVENTION

The present invention is a laser protection visor. This laser protection visor is formed in a shape which is an ellipsoidal segment. The ellipsoidal shape has its major axis disposed on the line joining the user's eyes. The foci of the ellipsoid are at least as far apart as the eyes of the user. A modulated index of refraction layer, such as a holographic optical element or a dielectric filter, is disposed on a substrate formed in this ellipsoidal shape.

This ellipsoidal shape serves to minimize the angles to the two eyes where protection is needed. The maximum angular protection is needed at the center of the visor with lesser angles of protection required at its periphery. This reduced angular protection at the periphery permits the visor to depart from a strictly ellipsoidal shape at the peripheral regions to allow, for example, better compatibility with existing helmets.

The ellipsoidal shape also serves to provide a "one size fits all" laser protection visor. If the visor is developed to provide protection for user's having the largest interpupillary distance, the protection is also provided for users having smaller interpupillary distances. This is because the user with the smaller interpupillary distance needs smaller protection angles for all points on the ellipsoidal segment.

In the preferred embodiment the modulated index of refraction layer is formed of a holographic optical element. A holographic optical element is formed by exposing a photosensitive medium to the interference between two laser beams. Upon development the interference fringes are captured in the form of varying indices of refraction. Dichromated gelatin or photopolymer and conventionally used as the photosensitive medium. In the case of the present invention, interference fringes are to be parallel to the surface of the layer. Such parallel fringes are formed by using as the second exposure beam the reflection from the far surface of the photosensitive layer.

Two examples are discussed in this application. In the first example the distance between the foci of the ellipsoidal segment is 75 millimeters. This requires a rejection angle at the corresponding expected wavelength of 30 degrees. The second example has a distance between the foci of 105 millimeters. This requires a rejection angle of only 22 degrees.

BRIEF DESCRIPTION OF THE DRAWINGS

These and other objects and aspects of the present invention will become clear from the following description of the invention taken in conjunction with the drawings, in which:

FIG. 7 illustrates a top view of an alternative embodiment of the laser protection visor having peripheral segments which deviate from the ellipsoidal shape.

DETAILED DESCRIPTION OF THE PREFERRED EMBODIMENT

Figure 1:
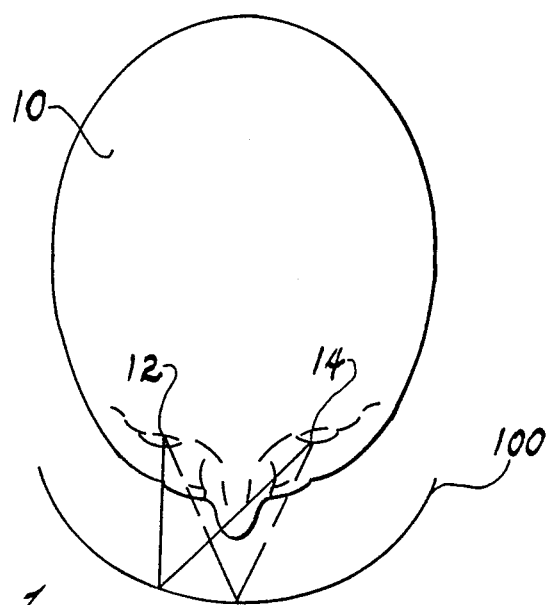
FIG. 1 illustrates a top view of the relationship of the laser protection visor of the present invention and the user's head.

Modulated index of refraction reflection filters which are geometrically concentric with the eye have been shown to yield a dramatic performance advantage as compared to standard spectacle lens geometries. This performance advantage is derived from keeping all eye threatening energy incident at the surface normal of the reflection filter. In geometries where eye-concentric spectacle substrates are not permitted, eye-centered holographic exposure have been shown to yield an optimum spatial frequency variation across the reflection filter surface, giving the best combination of single eye protection and visual transmittance. This technique is exemplified in the above-mentioned U.S. Pat. No. 4,830,441.

For laser protection visors, both eyes must be simultaneously protected at all points on the visor surface. A single, continuous, binocular surface cannot be simultaneously concentric to both eyes for viewing along the surface normal. However, the same basic design principle of eye-concentric substrates may be applied to binocular laser protection visors. The design principle of laser protection geometries is to keep all eye-threatening energy incident at the surface normal of the reflection filter. A corollary to this principle is if the viewing angle to the surface normal cannot be reduced to zero, it should at least be minimized. The binocular surface that best accomplishes this is an ellipsoid having its two foci coincident with the two eyes being protected. At any point on such an ellipsoid visor surface, the lines of sight of the two eyes are at equal and opposite angles to the surface normal. This minimizes the viewing angle of each eye. In fact, the viewing angle is greatest at the center line of this visor surface and is smallest for points farthest in azimuth from the center line. Thus full peripheral protection is achievable.

The most that can be reasonably expected from a single holographic optical element embodying the modulated index of refraction reflection filter using today's dichromated gelatin technology, for any single wavelength, is angular protection coverage for all rays within about 36 degrees to the surface normal. Current technology for photopolymer holographic elements yield even less effective bandwidth. It is known in the art that the angular protection coverage of a modulated index of refraction reflection filter is related to the index of refraction modulation within the element. Suppose the index of refraction is modulated within the element with a fringe spacing d. The index of refraction within the holographic optical element as a function of depth x is thus:

$$N = N_0 + \tfrac{1}{2}\Delta N \cos(2\pi x/d)$$

where N is the modulated index of refraction, $N^\circ$ is nominal index of refraction, and $\Delta N$ is the amplitude of the modulation of the index of refraction. This maximum angular coverage corresponds to the maximum refractive index modulation $\Delta N$ that we can impart to dichromated gelatin which is typically used in holographic optical elements before it begins to scatter or become hazy.

The following discussion of ellipsoidal visor design examples is predicated on an interpupillary distance (IPD) of 63.5 mm. This is very near the median IPD for U.S. military aviators. An 18 mm evaluation aperture said to be centered on the right eye is offset 31.75 mm horizontally from the vertical centerline of each visor. This 18 mm evaluation aperture takes into account the pupil aperture and the movement of the eye. The ellipsoid visor of the present invention can be designed such that "one size fits all," as will be shown below.

Figure 2:
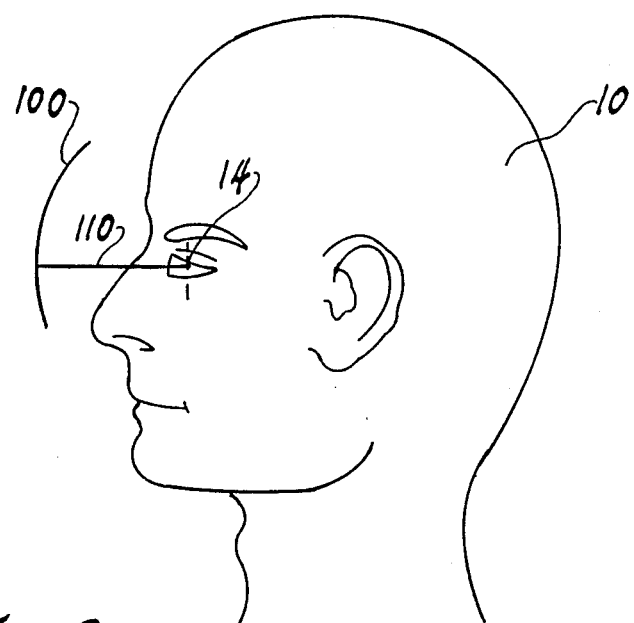
FIG. 2 illustrates a side view of the relationship of the laser protection visor of the present invention and the user's head.

FIGS. 1 and 2 illustrate the relationship of the laser protection visor of the present invention to the shape of the user's head. FIG. 1 shows a top view of the user's head 10, including right eye 12 and left eye 14. Laser protection visor 100 is disposed in front for eyes 12 and 14 of the user. The view of FIG. 1 shows laser protection visor 100 has a horizontal cross section which is a ellipse having foci at or near the expected eye positions. The view of FIG. 2 shows that laser protection visor 100 has a vertical cross section which is a circle centered about the line between the expected eye positions having a radius 110.

Considerable performance advantage can be gained letting the visor surface assume an ellipsoid shape. The optimum ellipsoid geometry has its foci nominally coincident with the two eyes, placing the two eyes' lines of sight at equal and opposite angles to the surface normal through any point on the visor. The maximum excursion of any line of sight from the surface normal is thereby minimized, yielding maximum eye protection.

Figure 3:
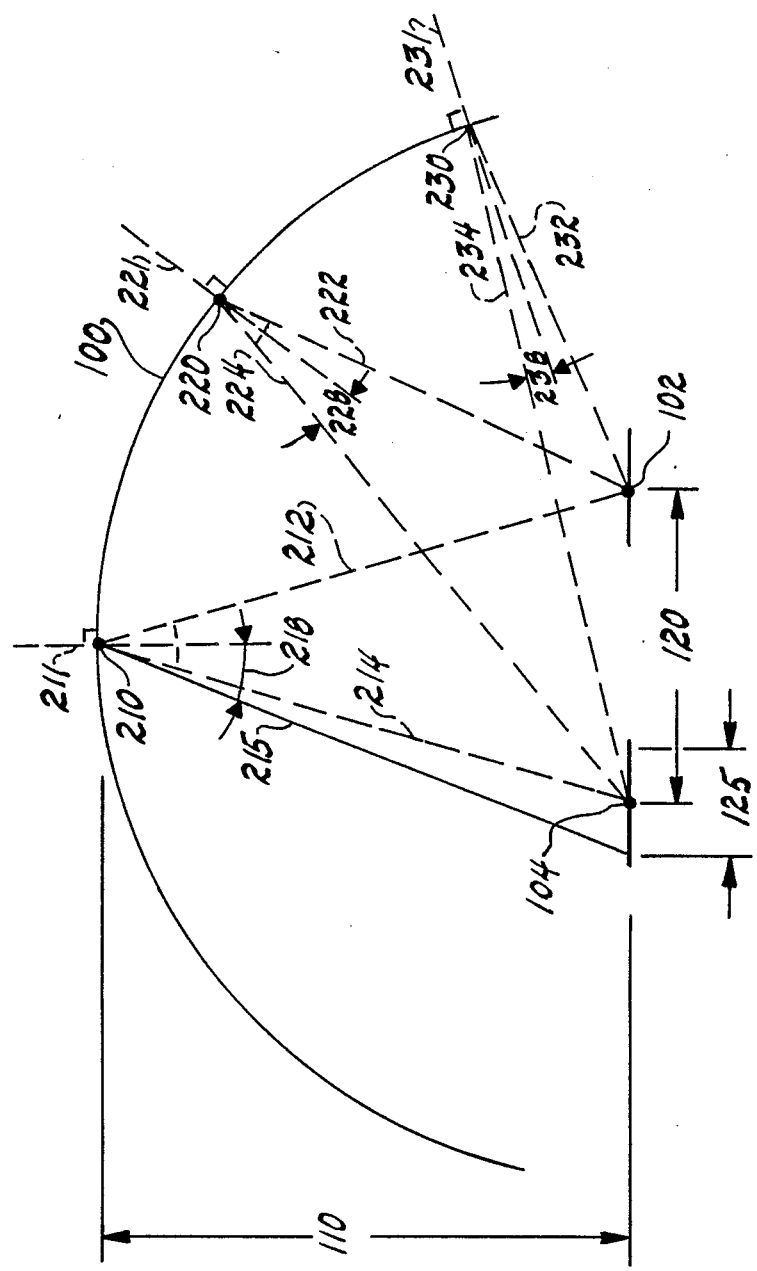
FIG. 3 illustrates a top view of the laser protection visor of the present invention in relation to the interpupillary distance between the user's eyes.

FIG. 3 illustrates the angle between the line of sight to each eye and the surface normal of laser protection visor 100. Point 102 corresponds to the expected position of the pupil of the right eye. Point 104 corresponds to the expected position of the pupil of the left eye. Distance 120 is the interpupillary distance which is approximately 63.5 mm. Distance 125 is the 18 mm evaluation aperture.

FIG. 3 illustrates the angle of incidence for each eye as compared with the surface normal for three points on the surface of visor 100. Point 210 is the center of visor 100. Normal 211 is the surface normal line at point 210. Line 212 is the line of sight through point 210 to point 102, representing the right eye. Line 214 is the line of sight to point 104 which corresponds to the left eye. The angle 218 between normal 211 and line 215 is the greatest angle through point 210 which can reach a portion of one of the 18 mm evaluation apertures. Note an equal angle occurs on the other side of normal 211. Point 220 is disposed about 45 degrees off the visor center. Normal 221 is the surface normal at point 220. Lines 222 and 224 are the line of sight to points 102 and 104, respectively. Angle 228 is the nominal angle of line of sight 224 to normal 221, which is the same as the angle to line of sight 222. Point 230 is disposed at the peripheral extreme of visor 100. Normal 231 is the surface normal at point 230. Lines 232 and 234 are the line of sight to points 102 and 104, respectively. Angle 238 is the nominal angle of line of sight 234 to normal 231, which is the same as the angle to line of sight 232.

FIG. 3 illustrates an important feature of the ellipsoidal shape of visor 100. On such an ellipsoid the maximum angle of required protection is highest at the centerline and decreases monotonically to zero at 90 degrees azimuth. This maximum angle of required protection is the same for both eyes. The protection criteria in this example is that no threat radiation shall enter a pair of 18 mm apertures centered at eye pupils 102 and 104. We can calculate the highest incidence angle at the centerline of the ellipsoid as:

$$\theta_{max} = \tan^{-1}\left(\frac{18 \text{ mm} + IPD}{2 D}\right)$$

where: $\theta_{max}$ is the maximum angle of incidence that can reach the 18 mm evaluation aperture; IPD is the interpupillary distance 120; and D is the vertex distance 110 from the line between points 102 and 104 and visor center 210.

The design examples that follow are compared at an IPD of 63.5 mm. The above equation indicates that a vertex distance D of 75 mm requires a maximum rejection angle of only about 28.5 degrees. This is within the maximum rejection angle achievable by the maximum index of refraction of conventional dichromated gelatin holographic optical elements.

The design equation relating vertex distance to required angular protection range suggests another iteration to the ellipsoid visor design. If the vertex distance is increased, the maximum viewing angle of incidence decreases. It is well known that modulated index of refraction filters such as the holographic optical filter of the present invention exhibit a shift of the rejection wavelength with increased angle of incidence from the optical normal. It is conventional to provide the angular rejection coverage desired by increasing the spectral width of the rejection notch. This has an adverse effect on visual see through. An ellipsoidal visor having a greater vertex distance would permit full-field eye protection with less angular bandwidth. This in turn permits a rejection notch of smaller spectral extent, thereby improving see through. An ellipsoid visor having 105 mm vertex distance would reduce the maximum rejection angle required to approximately 22 degrees.

Figure 4:
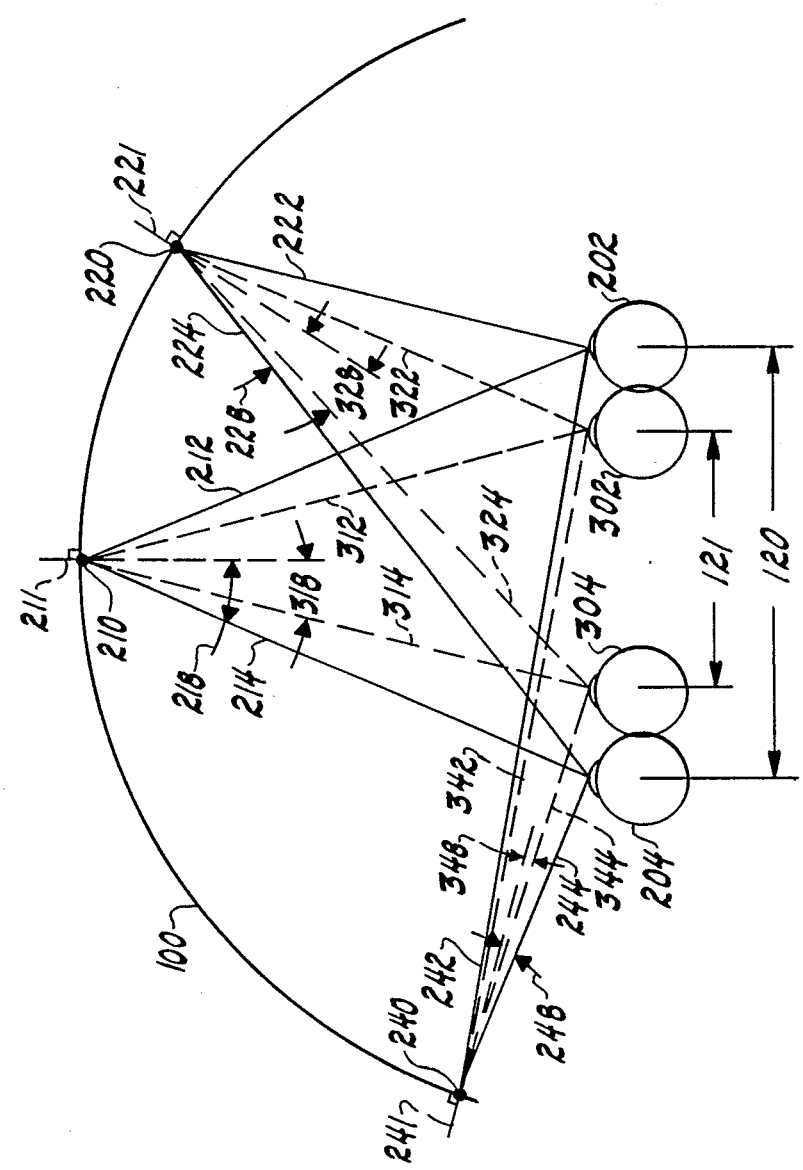
FIG. 4 illustrates a top view of the laser protection visor of the present invention in relation to users having differing interpupillary distances.

A major advantage of the ellipsoid visor, that has not yet been discussed, is the inherent potential for a "one size fits all" visor. That is, different holographic exposure and substrate geometries are not necessary to accommodate different IPD ranges, as might be the case with other visor shapes. As long as the visor is designed to perform adequately for the largest IPD user, all smaller IPD users will be fully protected as well. FIG. 4 helps to illustrate this concept. Shown in the major axis of the ellipsoid are points 202 and 204 that correspond to a large IPD defining the foci of the ellipsoid and points 302 and 304 corresponding to a smaller IPD. Line 312 is the line of sight through point 210 to point 302. Line 314 is the line of sight through point 210 to point 304. The angle 318 between normal 211 and line 314 is the greatest angle through point 210 which can reach either point 302 or 304. Lines 322 and 324 are the lines of sight through point 220 to points 302 and 304, respectively. Angle 328 is the nominal angle of line of sight 324 to normal 221, which is the greatest angle through point 220 which can reach either point 302 or 304. Point 240 is disposed at the peripheral extreme of visor 100. Normal 241 is the surface normal at point 240. Lines 242 and 244 are the line of sight to points 202 and 204, respectively. Angle 248 is the nominal angle of line of sight 244 to normal 241, which is the same as the angle to line of sight 242. Lines 342 and 344 are the line of sight to points 302 and 304, respectively. Angle 348 is the greatest angle through point 240 which can reach either point 302 or 304.

FIG. 4 illustrates the relative angles to the large IPD eyes 202 and 204 and the small IPD eyes 302 and 304. The surface normal, at any point on the ellipsoid, bisects the angles of incidence to that point from the foci corresponding to the large IPD eyes 202 and 204. The small IPD eyes 302 and 304 are disposed between large IPD eyes 202 and 204. Therefore, the angles of incidence from both points 302 and 304 corresponding to the smaller IPD eyes must lie closer to the surface normal than those of the large IPD eyes 202 and 204. The angles to points 302 and 304 may not be equal but these angles are both less than the angles to the corresponding large IPD eyes 202 and 204. Thus these angles must fall within the protection band designed for the larger IPD. It follows, then, that full protection for the largest IPD guarantees full protection for all IPD's, as long as the two eyes for any IPD are centered on the major axis of the visor 100.

The preferred embodiment of the present invention includes, as part of the visor/mounting assembly, features that identify the major axis for simple visual alignment to the pilot's pupils in both height and vertex distance. The visor could mechanically pivot about the major axis to locate over the pilot's breathing apparatus. Since the visor's optical performance is symmetric about this axis, different pivot positions for different pilots do not affect protection or visual transmission performance.

The modulated index of refraction layer of the present invention could be constructed of a multiple dielectric layer. This multiple dielectric layer may be formed by vapor depositing on the visor substrate surface multiple layers of differing index of refraction. The rejection bandwidth and rejection maximum angle required determine the respective dielectric layer depths and various indices of refraction.

In the preferred embodiment the modulated index of refraction layer is constructed of holographic optical elements. The holographic optical elements of the preferred embodiment of this invention are formed by capturing the interference pattern formed by the two beams of sufficiently coherent light in a photosensitive medium. In the case of reflection filters of the type used in the present invention, the processing of the exposed medium must convert the latent image into a modulated index of refraction. The fundamental holographic exposure parameters are exposure energy, exposure wavelength, exposure beam angle in the photosensitive medium, and changes in the thickness and bulk refractive index of the medium during processing. The exposure energy is adjusted, together with sensitization and process parameters, to achieve the correct index modulation amplitude for the desired spectral and angular bandwidth. The interactions between these parameters are known in the art and will not be further discussed.

Holographic optical elements having surface-conformal fringes are generally preferable for laser rejection filters. This preference is due to practical considerations because cosmetic defects and flare "rainbows" are difficult or impossible to eliminate in other types of holographic optical elements Surface-conformal holographic optical elements are fabricated by exposing a photosensitive medium to a single laser beam, and using a mirror in contact with the photosensitive medium to form the necessary second beam that interferes with the first.

Such holographic optical elements are often constructed with light at a different wavelength than the use wavelength. The ratio of the laser rejection notch wavelength to the holographic exposure wavelength is compensated by control of the exposure beam incidence angle, the net medium swelling and the refractive index change upon development. These factors combine to achieve the correct spatial frequency of the refractive index modulation. Larger wavelength ratios require increasing exposure beam angles according to the relationship:

$$\frac{\lambda_c}{\lambda_o} = \frac{S N_o}{N_e \cos \theta_e}$$

where $\lambda_c$ is the filter notch wavelength at normal angle of incidence, $\lambda_o$ is the holographic exposure wavelength, S is the net swelling or shrinkage of the photosensitive medium after exposure, $N_o$ is the bulk refractive index of the finished holographic optical element, $N_e$ is the bulk refractive index of the medium during exposure, and $\theta_e$ is the angle of incidence of the exposing beam to the surface normal inside the medium during exposure.

The photosensitive medium used in construction of holographic optical elements is typically dichromated gelatin or photopolymer. Dichromated gelatin is sensitive only at the shorter visible wavelengths and requires considerable exposure energy, typically limiting $\lambda_o$ to be either the 488 nm or 514.5 nm line of an argon ion laser. This material will require significant exposure beam angles to fabricate where a large wavelength ratio to any of the available exposure wavelengths is indicated. That ratio may be so large that the required exposure beam angle $\theta_e$ inside the medium is beyond the critical angle of total internal reflection. The exposure beam must therefore be coupled from air into the medium using a prism or tank to achieve the necessary angle.

The holographic optical element formed on the ellipsoid surface may be uniform with respect to the surface normal as discussed in the design examples. This requires that the exposure beam be incident at the same angle to the surface normal everywhere on the visor surface. This angle may exceed 45 degrees in the medium for protection against some threat wavelengths. Because the visor surface is not flat, a simple flat-surface prism arrangement cannot be used to obtain the necessary exposure angle.

Figure 5:
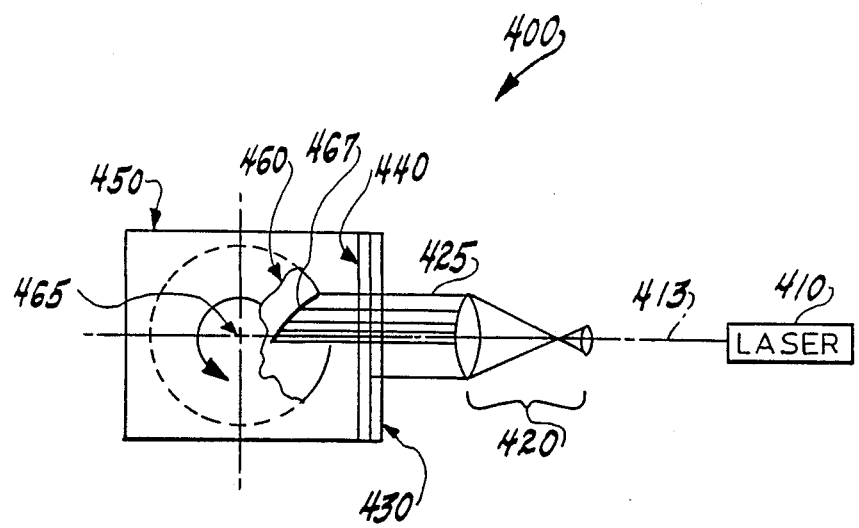
FIG. 5 illustrates a view of the manner of construction of the holographic optical element within the laser protection visor of the present invention.
Figure 6:
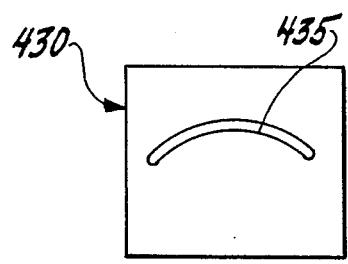
FIG. 6 illustrates the curved slit mask employed in construction of the holographic optical element within the laser protection visor of the present invention.

The preferred embodiment of the manner of wavelength-shifted construction of the laser protection visor is illustrated in FIGS. 5 and 6. This construction geometry takes advantage of a scanning exposure and the symmetry of the visor surface about its major axis. Construction system 400 includes: a laser 410 which generates a beam 415; beamforming optics 420 which produces a larger beam 425; a tank 450 holding an index matching fluid and the visor 460 with the photosensitive medium disposed on one surface. Light from beam 425 enters tank 450 via a slit window 430 which is disposed in front of a window 440 into the tank. As illustrated in FIG. 6, slit window 430 has a curved slit 435. The beamforming optics 420 and slit 435 illuminates a locus of points 467 on the visor 460 at a constant angle to the surface normal. The visor 460 is disposed on a scanning mechanism that pivots about the axis 465 of the ellipsoid, passing every point on its through the illuminated locus of points 467. In this way, all points on the visor 460 are exposed at the same internal angle of incidence as required. Since visor 460 is submerged in an index matching fluid in tank 450, there will be no total internal reflection or even Fresnel reflection to form the necessary second interfering beam. Therefore, the photosensitive medium is coated with an evaporated mirror to form the second beam upon exposure. This evaporated mirror coating is removed after exposure.

The design of the exposure system 400 referred to above involves several steps. First, the correct angle of incidence in the medium must be established to provide the correct notch wavelength using the appropriate exposure wavelength and material process parameters. The equation which describes the relationships that determine the correct angle is given above. Once this angle is determined, beamforming optics 420 with an appropriate slit 435 must be designed that will generate a locus of points 467 at that angle of incidence across the surface of the visor 460. This locus of points 467 must be of sufficient width such that the active area required of the holographic optical element is exposed when ellipsoid visor 460 is rotated about its axis of symmetry.

The beamforming optics 420 is designed using contour plots of constant incident angles at the surface of visor 460. The goal is a reasonable beamforming optics 420 that generates a contour at the appropriate angle with an appropriate shape and extent. The rays forming that contour are then traced back from the surface of visor 460 to the slit window 430 to define slit 435. For larger required angles of incidence at the surface of visor 460, a plane wave beam 425 may be adequate. The contour for that angle may be sufficiently wide to illuminate visor 460 upon rotation of the ellipsoid about its axis. However, if smaller angle of incidence angle were required for a different notch wavelength, the plane wave may not generate a sufficiently wide contour to cover the active area in visor 460. The beamforming optics 420 would in that case need to generate something other than a plane wave to provide a wider contour on the ellipsoid.

For smaller exposure angles of incidence, sufficiently below the critical angle, tank 450 may not be needed for its prism effect and the exposure may be performed in air. The air exposure design process is the same, however, using contour plots of incidence angle to arrive at an acceptable beamforming optics 420 and slit 435.

In some cases the design of laser protection visor 100 does not need one holographic optical element for each threat wavelength. In some cases two or more threat wavelengths may be so close that a single holographic optical element may reject them all. This requires that the holographic optical element design have sufficient spectral bandwidth to cover each of these threat wavelengths for all needed angles of incidence. Because the ellipsoidal geometry of laser protection visor 100 limits the needed angular protection coverage, it is more likely that a single holographic optical element can provide protection for plural threat wavelengths than in other geometries.

FIG. 7 illustrates an alternative embodiment of the present invention. The laser protection visor 100 of FIG. 7 is constructed in three segments. The first segment is an ellipsoidal center segment 150. This ellipsoidal center segment 150 has foci 102 and 104 and a vertex distance of 110. Laser radiation entering ellipsoidal center segment 150 through center point 210 has a maximum angle with respect to the perpendicular 211 that can enter either eye of 218. There are two peripheral segments 160 and 170 which are symmetrically disposed on either side of the user. Peripheral segments 160 and 170 deviate from the ellipsoidal shape of ellipsoidal center segment 150 (shown in dashed lines). This deviation from ellipsoidal shape could be for better accommodation of a standard helmet or the like.

The maximum angle to the perpendicular within peripheral segments 160 and 170 is through point 251. This maximum angle 258 is the angle between perpendicular 251 and line 256 which just enters the right eye. Peripheral segments 160 and 170 have been constructed so that this maximum angle is still less than the angle 218 at the center of laser protection visor 100. Thus the modulated index of refraction filter within laser protection visor 100 does not need to cover a greater angular bandwidth than that of angle 218. This is advantageous because the filter element does not need to be changed when providing the peripheral segments to accommodate the helmet shape.

It has been demonstrated that an ellipsoid surface having foci corresponding to the two eye positions allows full eye protection in a minimum holographic angular and spectral bandwidth. This is due to the fact that the line of sight of each eye through all points on the visor is restricted to a relatively small angle with respect to the surface normal on such an ellipsoid in comparison to a standard aviator's helmet visor. As the vertex distance or eye relief of the ellipsoid design is increased, the maximum angle of incidence is reduced further, allowing a narrower bandwidth holographic optical element accompanied by an increased visual transmittance. It is also significant that the ellipsoid concept allows a "one size fits all" holographic visor that provides full eye protection for all interpupillary distances.

I claim:

1. A laser protection visor for a user having an expected interpupillary distance for protection against at least one laser threat each having a corresponding expected wavelength, said laser protection visor comprising:
   a transparent substrate formed in a substantially ellipsoidal segment, said ellipsoidal segment having foci disposed at least as far apart as the expected interpupillary distance, said transparent substrate disposed so that the major axis of said ellipsoidal segment is substantially coincident with a line connecting the center of the user's eyes;
   at least one modulated index of refraction layer disposed on one surface of said transparent substrate, each modulated index of refraction layer having embedded therein a spatially modulated index of refraction disposed everywhere parallel to the surface of said modulated index of refraction layer for forming a reflection filter element having a bandwidth including a corresponding expected wavelength thereby forming a virtual mirror surface everywhere coincident with said transparent substrate.

2. The laser protection visor as claimed in claim 1, wherein:
   said at least one modulated index of refraction layer is constructed with a maximum rejection angle at the expected wavelength given by:

$$\theta_{rej} = \tan^{-1}\left(\frac{A + IPD}{2D}\right)$$

where: $\theta_{rej}$ is the maximum rejection angle at the expected wavelength; A is the effective aperture of each eye of the user; IPD is the interpupillary distance of the user; and D is the vertex distance from the line between the user's eyes and the visor center.

3. The laser protection visor as claimed in claim 2, wherein:
   said vertex distance of said ellipsoidal segment is 75 millimeters; and
   each of said at least one modulated index of refraction layer is constructed to have a maximum rejection angle at the corresponding expected wavelength of 30 degrees.

4. The laser protection visor as claimed in claim 2, wherein:
   said vertex distance of said ellipsoidal segment is 105 millimeters; and
   each of said at least one modulated index of refraction layer is constructed to have a maximum rejection angle at the corresponding expected wavelength of 22 degrees.

5. The laser protection visor as claimed in claim 1, wherein the at least one laser threat includes a plurality of laser threats, and wherein:
   each of said at least one modulated index of refraction layer forms a reflection filter element having a bandwidth including a plurality of corresponding expected wavelengths.

6. The laser protection visor as claimed in claim 1, wherein:
each of said at least one modulated index of refraction layers consists of a holographic optical element.

7. The laser protection visor as claimed in claim 1, wherein:
each of said at least one modulated index of refraction layers consists of a multiple layer dielectric.

8. The laser protection visor for a user having an expected interpupillary distance for protection against at least one laser threat each having a corresponding expected wavelength, said laser protection visor comprising:
a transparent substrate formed having a substantially ellipsoidal center segment, said ellipsoidal center segment having foci disposed at least as far apart as the expected interpupillary distance, and having peripheral segments which deviate from an ellipsoidal shape, said transparent substrate disposed so that the major axis of said ellipsoidal center segment is substantially coincident with a line connecting the center of the user's eyes;
at least one modulated index of refraction layer disposed on one surface of said transparent substrate, each modulated index of refraction layer having embedded therein a spatially modulated index of refraction disposed everywhere parallel to the surface of said modulated index of refraction layer for forming a reflection filter element having a bandwidth including a corresponding expected wavelength thereby forming a virtual mirror surface everywhere coincident with said transparent substrate.

9. The laser protection visor as claimed in claim 8, wherein:
said at least one modulated index of refraction layer is constructed with a maximum rejection angle at the expected wavelength given by:

$$\theta_{rej} = \tan^{-1}\left(\frac{A + IPD}{2D}\right)$$

where: $\theta_{rej}$ is the maximum rejection angle at the expected wavelength; A is the effective aperture of each eye of the user; IPD is the interpupillary distance of the user; and D is the vertex distance from the line between the user's eyes and the visor center.

10. The laser protection visor as claimed in claim 9, wherein:
said vertex distance of said ellipsoidal segment is 75 millimeters; and
each of said at least one modulated index of refraction layer is constructed to have a maximum rejection angle at the corresponding expected wavelength of 30 degrees.

11. The laser protection visor as claimed in claim 9, wherein:
said vertex distance of said ellipsoidal segment is 105 millimeters; and
each of said at least one modulated index of refraction layer is constructed to have a maximum rejection angle at the corresponding expected wavelength of 22 degrees.

12. The laser protection visor as claimed in claim 8, wherein the at least one laser threat includes a plurality of laser threats, and wherein:
each of said at least one modulated index of refraction layer forms a reflection filter element having a bandwidth including a plurality of corresponding expected wavelengths.

13. The laser protection visor as claimed in claim 8, wherein:
each of said at least one modulated index of refraction layers consists of a holographic optical element.

14. The laser protection visor as claimed in claim 8, wherein:
each of said at least one modulated index of refraction layers consists of a multiple layer dielectric.

15. The laser protection visor as claimed in claim 8, wherein:
said peripheral segments which deviate from an ellipsoidal shape in a manner whereby the maximum angle to the perpendicular of the transparent substrate of a line through any portion of said peripheral segments to either eye of the user is no greater than the maximum angle to the perpendicular of the transparent substrate of a line through the center of said ellipsoidal center segment to either eye of the user.

* * * * *

UNITED STATES PATENT AND TRADEMARK OFFICE
CERTIFICATE OF CORRECTION

PATENT NO. : 4,978,182

DATED : December 18, 1990

INVENTOR(S) : James M. Tedesco

It is certified that error appears in the above-identified patent and that said Letters Patent is hereby corrected as shown below:

Column 1, line 12, after "detection", delete --,--;

Column 2, line 18, after "teaches", insert --a--;

Column 3, line 8, "and" should be --is--;

Column 4, line 33, "$\tfrac{1}{2}N$" should be --$\Delta N$--;

Column 4, line 35, "N°" should be --$N_0$--;

Column 7, line 35, after "elements", insert --.--.

Signed and Sealed this

Twenty-third Day of June, 1992

Attest:

DOUGLAS B. COMER

*Attesting Officer*    *Acting Commissioner of Patents and Trademarks*